US009193917B2

(12) United States Patent
Hayasaka

(10) Patent No.: US 9,193,917 B2
(45) Date of Patent: Nov. 24, 2015

(54) METHOD FOR ESTIMATING CONTENT OF FINE PARTICLES IN SLURRY AND PROCESS FOR PRODUCING HYDROCARBON OIL

(75) Inventor: Kazuaki Hayasaka, Tokyo (JP)

(73) Assignees: JAPAN OIL. GAS AND METALS NATIONAL CORPORATION, Tokyo (JP); JX NIPPON OIL & ENERGY CORPORATION, Tokyo (JP); COSMO OIL CO., LTD., Tokyo (JP); INPEX CORPORATION, Tokyo (JP); JAPAN PETROLEUM EXPLORATION CO., LTD., Tokyo (JP); NIPPON STEEL & SUMIKIN ENGINEERING CO., LTD., Tokyo (JP)

( * ) Notice: Subject to any disclaimer, the term of this patent is extended or adjusted under 35 U.S.C. 154(b) by 54 days.

(21) Appl. No.: 14/007,898

(22) PCT Filed: Mar. 26, 2012

(86) PCT No.: PCT/JP2012/057772
§ 371 (c)(1),
(2), (4) Date: Dec. 2, 2013

(87) PCT Pub. No.: WO2012/133324
PCT Pub. Date: Oct. 4, 2012

(65) Prior Publication Data
US 2014/0080926 A1    Mar. 20, 2014

(30) Foreign Application Priority Data
Mar. 31, 2011  (JP) ................. 2011-080619

(51) Int. Cl.
C07C 27/00    (2006.01)
G01N 31/10    (2006.01)
C10G 2/00     (2006.01)
G01N 21/59    (2006.01)
G01N 15/06    (2006.01)
C10G 31/00    (2006.01)
G01N 15/02    (2006.01)
G01N 15/04    (2006.01)
B01J 23/46    (2006.01)
G01N 15/00    (2006.01)
B01J 23/745   (2006.01)
B01J 23/75    (2006.01)
B01J 23/755   (2006.01)
B01J 23/89    (2006.01)

(52) U.S. Cl.
CPC .............. *C10G 2/344* (2013.01); *B01J 23/462* (2013.01); *C10G 2/332* (2013.01); *C10G 2/341* (2013.01); *C10G 31/00* (2013.01); *G01N 15/0205* (2013.01); *G01N 15/04* (2013.01); *G01N 15/06* (2013.01); *G01N 21/59* (2013.01); *B01J 23/745* (2013.01); *B01J 23/75* (2013.01);

*B01J 23/755* (2013.01); *B01J 23/8913* (2013.01); *G01N 2015/0053* (2013.01)

(58) Field of Classification Search
CPC ........ C10G 2/341; C10G 2/332; C10G 31/00; G01N 15/04; G01N 15/0205; G01N 15/06; G01N 21/59; G01N 2015/0053
USPC ............................................. 518/700; 436/37
See application file for complete search history.

(56) References Cited

U.S. PATENT DOCUMENTS

| 3,315,066 | A  | 4/1967 | Muta et al. |
| 3,449,567 | A  | 6/1969 | Olivier et al. |
| 4,853,551 | A  | 8/1989 | Wagner et al. |
| 4,920,550 | A  | 4/1990 | Olivier et al. |
| 7,378,452 | B2 | 5/2008 | Long et al. |
| 7,488,760 | B2 | 2/2009 | Vogel |
| 2002/0128330 | A1 | 9/2002 | Anderson |
| 2004/0014825 | A1 | 1/2004 | Hensman |
| 2005/0209350 | A1 | 9/2005 | Espinoza et al. |
| 2007/0161715 | A1 | 7/2007 | Long et al. |
| 2007/0197667 | A1 | 8/2007 | Vogel |
| 2008/0015266 | A1 | 1/2008 | Yakobson et al. |
| 2011/0028574 | A1 | 2/2011 | Woo et al. |

FOREIGN PATENT DOCUMENTS

| CN | 1246267   | 3/2006 |
| CN | 100404118 | 7/2008 |

(Continued)

OTHER PUBLICATIONS

International Preliminary Report on Patentability for PCT/JP2012/057772, mailed on Oct. 17, 2013.
International Search Report for PCT/JP2012/057772, mailed on Jun. 5, 2012.
Office Action for CN Patent Application No. 201280013913.6 mailed Dec. 10, 2014.
Extended European Search Report for European Patent Application No. 12763046.5 mailed Sep. 5, 2014.
Office Action of JP Patent Application No. 2011-080619 mailed Jan. 27, 2015.
Office Action for Chinese Patent Application No. 201280013913.6, which is dated Jul. 29, 2014.

*Primary Examiner* — Jafar Parsa
(74) *Attorney, Agent, or Firm* — Greenblum & Bernstein, P.L.C.

(57) ABSTRACT

A method for estimating a particulate content in a slurry of the present invention is a method for estimating a content of particulates having a predetermined particle size or less in a slurry with solid particles dispersed in hydrocarbons including a wax, the method including, based on a correlation between a visible light transmittance and a content of solid particles having the predetermined particle size or less at a temperature at which hydrocarbons including a wax are liquefied when the solid particles having the predetermined particle size or less are dispersed in the hydrocarbons, estimating a content of particulates having the predetermined particle size or less in the slurry from a visible light transmittance of a supernatant part when the slurry is left to stand at the temperature.

8 Claims, 3 Drawing Sheets

(56) References Cited

FOREIGN PATENT DOCUMENTS

| | | |
|---|---|---|
| CN | 101959575 | 1/2011 |
| JP | H01-259247 | 10/1989 |
| JP | H08-069132 | 3/1996 |
| JP | 2004-509935 | 4/2004 |
| JP | 2005-331492 | 12/2005 |
| JP | 2006-205111 | 8/2006 |
| JP | 2007-516065 | 6/2007 |
| JP | 2008-001909 | 1/2008 |
| JP | 2009-522410 | 6/2009 |
| WO | 02/26667 | 4/2002 |
| WO | 2007/079031 | 7/2007 |
| WO | 2009/107927 | 9/2009 |
| WO | 2011/034036 | 3/2011 |

METHOD FOR ESTIMATING CONTENT OF FINE PARTICLES IN SLURRY AND PROCESS FOR PRODUCING HYDROCARBON OIL

TECHNICAL FIELD

The present invention relates to a method for estimating a particulate content in a slurry and a process for producing a hydrocarbon oil using the same.

BACKGROUND ART

As a process for producing a hydrocarbon oil used as raw materials for liquid fuel products such as a kerosene and gas oil, a method using a Fischer-Tropsch synthesis reaction (hereinafter, also referred to as the "FT synthesis reaction" in some cases) in which synthesis gas containing carbon monoxide gas (CO) and hydrogen gas ($H_2$) as main components is used as raw material gas is known.

As a process for producing a hydrocarbon oil by the FT synthesis reaction, for example, Patent Literature 1 described below discloses a method using a slurry bubble column reactor (a bubble column type slurry bed reactor) in which synthesis gas is blown into a slurry (hereinafter, simply also referred to as the "slurry" in some cases) with particles of a solid catalyst having activity to the FT synthesis reaction (hereinafter, also referred to as the "FT synthesis catalyst" in some cases) suspended in liquid hydrocarbons.

In this method, a hydrocarbon oil is produced by a reaction system provided with a reactor that performs the FT synthesis reaction with accommodating the slurry and having a gaseous phase portion in an upper portion of the slurry (slurry bubble column reactor); a conduit that blows the synthesis gas into a bottom portion of the reactor; a catalyst separator equipped with a filter, that separates catalyst particles from the slurry in the reactor; a conduit that takes out liquid hydrocarbons (heavy liquid hydrocarbons) synthesized in the reactor and passing through the filter; and a mechanism that sends back a part of the liquid hydrocarbons taken out via this conduit to the filter and washes the filter. In the mechanism that washes the filter, a so-called "backwashing" manner is adopted in which the liquid hydrocarbons (heavy liquid hydrocarbons) taken out via the conduit are, for example, periodically flowed to the filter in a direction opposite to the flowing direction of the liquid hydrocarbons when the catalyst particles are separated from the slurry, and the catalyst particles captured by the filter are returned into the slurry again.

CITATION LIST

Patent Literature

[Patent Literature 1] National Publication of International Patent Application No. 2007-516065

SUMMARY OF INVENTION

Technical Problem

However, as the slurry bubble column reactor is operated to perform the FT synthesis reaction, clogging of the filter may occur. It has been revealed by examination by the present inventors that a part of the FT synthesis catalyst particles is gradually reduced to particulates due to friction between the FT synthesis catalyst particles, friction with an inner wall or the like of the reactor, or hydrothermal damage by the FT synthesis reaction, and these catalyst particulates are contained in the slurry in a large amount, thereby easily causing the clogging of the filter.

If the backwashing of the filter is performed with high frequency, the clogging of the filter can be more certainly removed, and, on the other hand, a part of the heavy liquid hydrocarbons which are a product of the FT synthesis reaction is returned to the reactor in the backwashing. Therefore, the higher frequency of the backwashing is not preferable from the viewpoint of productivity. Further, since the heavy liquid hydrocarbons returned to the reactor form a slurry again, and are filtered by the filter and taken out, the higher frequency of the backwashing increases an amount of the slurry passing through the filter per unit time, namely, increases a load of the filter. In addition, in order to cover a large load of the filter, a filter with a large filter area is needed to result in excessive facility, thereby increasing facility cost and maintenance cost. Therefore, the frequency of the backwashing is needed to be lowered as much as possible.

Meanwhile, since the clogging of the filter proceeds to pose a problem for operation itself of the slurry bubble column reactor, it is necessary to heighten the frequency of the backwashing and to remove the clogging of the filter when it is judged that the clogging of the filter has proceeded to a certain level. Although a degree of the clogging of the filter is usually found by measurement of a differential pressure before and after the filter, the clogging of the filter by the catalyst particulates is not removed and further proceeds in some cases even though the frequency of the backwashing is heightened after increase in the differential pressure is detected. Therefore, for responding to this, it has been considered to predict the clogging of the filter at an early stage before the differential pressure of the filter is increased, thereby determining the frequency of the backwashing.

In addition, a part of the catalyst particulates passes through the filter of the catalyst separator and accompanies with the heavy liquid hydrocarbons to be taken out. In order to capture these catalyst particulates which have passed through the filter, a filtering apparatus provided with a filter having smaller openings than the filter of the catalyst separator is generally provided downstream of the catalyst separator. This filter of the filtering apparatus also tends to be clogged like the filter of the catalyst separator if a concentration of the catalyst particulates in the reactor is increased.

As a method for predicting the clogging of these filters, there is considered a method for finding a catalyst particulate content in a slurry, namely, for example, a method in which a catalyst particulate content in a slurry is periodically measured and, when this content exceeds a predetermined value, the frequency of the backwashing is heightened. However, in a case of being a slurry whose medium is a component like a wax that is solidified at room temperature, a composition of solid particles in the slurry is not easily found with certainty for the following reasons.

As a method for analyzing a composition of solid particles dispersed in the slurry, there is considered, for example, a method in which the slurry is heated in air to incinerate and thus remove hydrocarbons, only catalyst particles are recovered as ash, a particle size distribution of the resulting catalyst particles is measured by a Coulter counter or the like (hereinafter, referred to as the "incineration method".). In this incineration method, since heating as a pretreatment is performed over a period of several hours and furthermore the catalyst particles are heated to be adhered to one another, a particle size distribution of the catalyst particles does not necessarily certainly show a particle size distribution in the slurry in some cases. As another method, there is considered a method in which hydrocarbons in a slurry are melted by a heated solvent, catalyst particles are filtered by hot filtration, and a particle size distribution of the resulting catalyst particles is measured by a Coulter counter or the like (hereinafter, referred to as the "solvent washing method".). In this solvent washing method, while washing by a large amount of a heated solvent as a pretreatment is needed, it is difficult to obtain catalyst particles in which hydrocarbons are sufficiently removed. In this way, in conventional methods, it was difficult to perform a rapid measurement and furthermore there was also a problem of reliability of measurement results.

The present invention has been made in consideration of such circumstances, and an object of the present invention is to provide a method which can simply and accurately estimate a content of particulates having a predetermined particle size or less in a slurry with solid particles dispersed in hydrocarbons including a wax, and a process for producing a hydrocarbon oil, which can prevent a filter for separating a catalyst from a slurry from clogging in a slurry bubble column reactor for performing the FT synthesis reaction to efficiently produce a hydrocarbon oil.

Solution to Problem

In order to solve the problems above, the present invention provides a method for estimating a content of particulates having a predetermined particle size or less in a slurry with solid particles dispersed in hydrocarbons including a wax, the method comprising, based on a correlation between a visible light transmittance and a content of solid particles having the predetermined particle size or less at a temperature at which hydrocarbons including a wax are liquefied when the solid particles having the predetermined particle size or less are dispersed in the hydrocarbons, estimating a content of particulates having the predetermined particle size or less in the slurry from a visible light transmittance of a supernatant part when the slurry is left to stand at the temperature.

According to the method of the present invention, the correlation is preliminarily determined and thereby the content of particulates having a predetermined particle size or less in the slurry can be accurately estimated by a simple method in which a measurement sample taken from the slurry is left to stand at the above-described temperature for about 10 minutes and the visible light transmittance of the supernatant part is measured.

The solid particle may be a Fischer-Tropsch synthesis catalyst in which cobalt and/or ruthenium is supported by an inorganic oxide catalyst support.

In the case where the solid particle is the Fischer-Tropsch synthesis catalyst in which cobalt and/or ruthenium is supported by an inorganic oxide catalyst support, a content of catalyst particulates having a predetermined particle size or less in a slurry in a slurry bubble column reactor for performing the FT synthesis reaction can be simply and accurately estimated. This makes it possible to effectively prevent a filter for separating a catalyst from a slurry from clogging in the reactor.

In this way, according to the present invention, a cumbersome pretreatment needed in the above-mentioned incineration method and solvent washing method need not to be performed, thereby not only making it possible to considerably shorten a measurement time and to rapidly obtain a measurement result, but also making it possible to solve a problem about measurement precision which is considered to be due to adhesion between particles and unsatisfactory removal of hydrocarbons which cause problems in the above-mentioned methods.

The present invention also provides a process for producing a hydrocarbon oil by a Fischer-Tropsch synthesis reaction using a slurry bubble column reactor that retains a slurry containing catalyst particles and liquid hydrocarbons inside thereof and that has a gaseous phase portion at an upper portion of the slurry, comprising a step of flowing the slurry through a filter provided inside and/or outside of the reactor to separate the slurry into catalyst particles and heavy liquid hydrocarbons and to take out the heavy liquid hydrocarbons; a backwashing step of flowing liquid hydrocarbons through the filter in a direction opposite to the flowing direction of the slurry to return the catalyst particles accumulated on the filter into a slurry bed in the reactor; and a monitoring step of estimating a content of particulates having a predetermined particle size or less in the slurry by the method for estimating a particulate content in a slurry according to the present invention.

The monitoring step is included in the process for producing a hydrocarbon oil of the present invention, thereby making it possible to simply and accurately estimate the content of particulates having a predetermined particle size or less in a slurry, and to perform the backwashing step with an appropriate frequency based on such a particulate content. This can prevent the filter for a slurry in the slurry bubble column reactor for performing the FT synthesis reaction from clogging, to efficiently produce a hydrocarbon oil.

In the process for producing a hydrocarbon oil of the present invention, a frequency of performing the backwashing step is preferably determined based on the estimation result of a content of particulates having a predetermined particle size or less in the slurry obtained in the monitoring step.

It is to be noted that the frequency herein referred means an interval (time) for performing the backwashing per one filter element.

In addition, in the process for producing a hydrocarbon oil of the present invention, a time for replacing or washing the filter for removing the particulates accompanied with the heavy liquid hydrocarbons taken out is preferably determined based on the estimation result of a content of particulates having a predetermined particle size or less in the slurry obtained in the monitoring step.

Advantageous Effects of Invention

According to the present invention, a method which can simply and accurately estimate a content of particulates having a predetermined particle size or less in a slurry with solid particles dispersed in hydrocarbons including a wax, and a process for producing a hydrocarbon oil, which can prevent a filter for separating a catalyst from a slurry and a filter for removing particulates accompanied with heavy liquid hydrocarbons having passed through the filter for separating and taken out, from clogging in a slurry bubble column reactor for performing the FT synthesis reaction, to efficiently produce a hydrocarbon oil can be provided.

DESCRIPTION OF EMBODIMENTS

Figure 1:
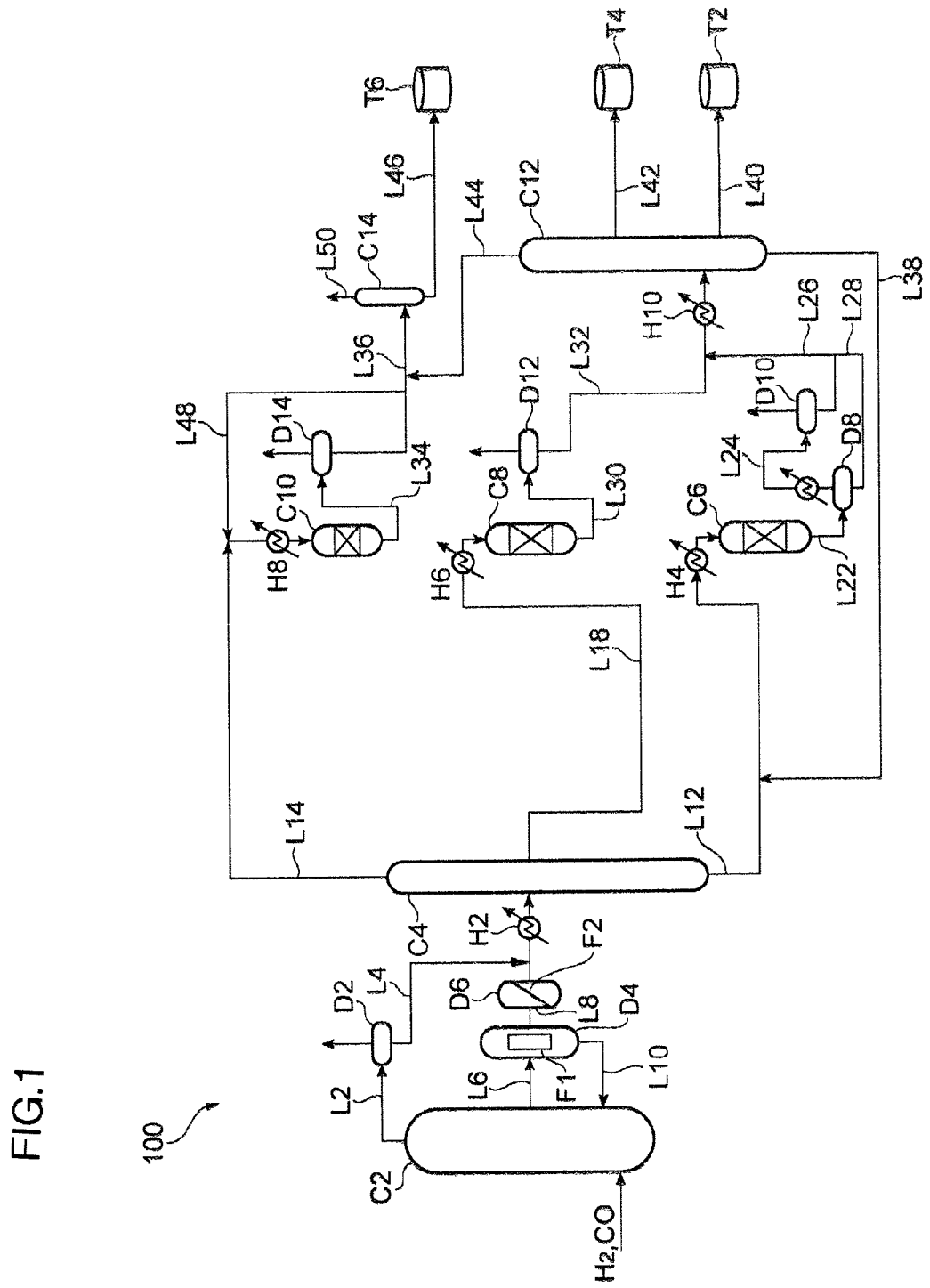
FIG. 1 is a schematic view showing one embodiment of a system for producing a hydrocarbon oil in which a process for producing a hydrocarbon oil according to the present invention is performed.

Hereinafter, a process for producing a hydrocarbon oil of the present invention using a method for estimating a particulate content in a slurry of the present invention will be described with reference to FIG. 1. FIG. 1 is a schematic view showing one embodiment of a system for producing a hydrocarbon oil in which the process for producing a hydrocarbon oil according to the present invention is performed. Here, same reference numerals will be given to same or identical components.

A system for producing a hydrocarbon oil 100 used in the present embodiment is a plant facility for performing a GTL process that converts a hydrocarbon raw material such as natural gas into a base stock for liquid fuel (hydrocarbon oil) such as gas oil, kerosene, and naphtha. The system for producing a hydrocarbon oil 100 of the present embodiment mainly includes a reformer (not shown), a slurry bubble column reactor C2, a removal line L6, a catalyst separator D4, a sending-back pipe L10, a first fractionator C4, a wax fraction hydrocracking apparatus C6, a middle distillate hydrotreating apparatus C8, a naphtha fraction hydrotreating apparatus C10 and a second fractionator C12. The removal line L6 is connected to a central portion of the slurry bubble column reactor C2 and transfers a slurry containing catalyst particles and heavy liquid hydrocarbons including a wax taken out from the reactor C2 to the catalyst separator D4. The catalyst separator D4 includes a filter F1 provided inside thereof, separates the slurry transferred by the removal line L6 into catalyst particles and heavy liquid hydrocarbons, and sends back the catalyst particles and a part of the hydrocarbons which are separated, from the sending-back pipe L10 to the reactor C2. A backwashing liquid tank (not shown) temporarily stores a part of the heavy liquid hydrocarbons separated from the catalyst particles by the catalyst separator D4, and allows the stored heavy liquid hydrocarbons to be flowed through the filter F1 of the catalyst separator D4 in a direction opposite to the flowing direction upon filtration of the slurry, thereby making it possible to return the catalyst particles accumulated on the filter F1 from the sending-back pipe L10 into a slurry bed in the reactor C2. In addition, a line L2 for taking out a gaseous component from a gaseous phase portion of the reactor C2 is connected to a top portion of the reactor C2, and a cooler E2 and a gas liquid separator D2 are connected to the line L2. Here, the "line" means a piping for transferring a fluid.

In the present embodiment, the slurry is separated to the catalyst particles and the heavy liquid hydrocarbons by the catalyst separator D4 provided outside of the reactor C2, but an aspect can be also adopted in which the slurry is allowed to be flown through a filter provided inside of the reactor C2 to be separated into the catalyst particles and the heavy liquid hydrocarbons, and the heavy liquid hydrocarbons are taken out. Further, a catalyst separator provided outside of the reactor C2 and a catalyst separator provided inside of the reactor C2 may be also used simultaneously.

The process for producing a hydrocarbon oil according to the present embodiment using the production system 100 include the following Steps S1 to S11.

In Step S1, natural gas as a hydrocarbon raw material is reformed in the reformer (not shown) to produce synthesis gas containing carbon monoxide gas and hydrogen gas.

In Step S2, in the slurry bubble column reactor C2, an FT synthetic oil is synthesized from the synthesis gas obtained in Step S1 by the FT synthesis reaction using a FT synthesis catalyst.

In Step S3, a slurry containing heavy liquid hydrocarbons including a wax and a FT synthesis catalyst of the FT synthetic oil synthesized in Step S2 is flown through the filter F1 in the catalyst separator D4 provided outside of the reactor C2 to be separated into catalyst particles and heavy liquid hydrocarbons, and the heavy liquid hydrocarbons are taken out.

Meanwhile, unreacted synthesis gas in the slurry (unreacted synthesis gas) and a gaseous component including light hydrocarbons which are produced by the FT synthesis reaction and are gaseous under the condition within the reactor C2 are taken out from the gaseous phase portion of reactor C2 by the line L2, the gaseous component is cooled in the cooler (not shown) to condense a part of the light hydrocarbons, and light liquid hydrocarbons separated in the gas liquid separator D2 mix with the heavy liquid hydrocarbons by a line L4.

In Step S4, in the first fractionator C4, a mixture of the heavy liquid hydrocarbons and the light liquid hydrocarbons obtained in Step S3 is fractionated into a raw naphtha fraction (with a boiling point of lower than 150° C.), a raw middle distillate (with a boiling point of about 150 to 360° C.) and a raw wax fraction (with a boiling point of higher than about 360° C.). Here, the raw naphtha fraction, the raw middle distillate and the raw wax fraction each refer to each fraction which does not undergo hydrotreating or hydrocracking processing and contains olefins and oxygen-containing compounds (such as alcohols) as impurities other than saturated aliphatic hydrocarbons as a main component.

In Step S5, hydrocracking of the raw wax fraction separated in Step S4 is performed in the wax fraction hydrocracking apparatus C6.

In Step S6, hydrotreating of the raw middle distillate separated in Step S4 is performed in the middle distillate hydrotreating apparatus C8.

In Step S7, hydrotreating of the raw naphtha fraction separated in Step S4 is performed in the naphtha fraction hydrotreating apparatus C10. Further, the hydrotreated naphtha fraction is fractionated in a naphtha stabilizer C14 and naphtha (GTL-naphtha) that is a product of the GTL process is recovered.

In Step S8, a mixture of a hydrocracking product of the raw wax fraction and a hydrotreated product of the raw middle distillate is fractionated in the second fractionator C12. By the fractionation, a base stock for gas oil (GTL-gas oil) and a base stock for kerosene (GTL-kerosene) that are products of the GTL process are recovered. Further, a light fraction corresponding to the naphtha fraction is fed to the naphtha stabilizer C14.

In Step S9, a part of a slurry containing the FT synthetic oil synthesized in Step S2 and the FT synthesis catalyst is taken, and a content of particulates having a predetermined particle size or less in the slurry is estimated by the method for estimating a particulate content in a slurry according to the present invention.

In Step S10, backwashing is performed, in which liquid hydrocarbons are flown through the filter F1 in the catalyst separator D4 in a direction opposite to the flowing direction of the slurry to return the catalyst particles accumulated on the filter to a slurry bed in the reactor C2. In the present embodiment, a frequency of performing the backwashing step is determined based on a result of Step S9.

In Step S11, the catalyst particles are separated by the catalyst separator D4, and at least one part of the particulates accompanied with the heavy liquid hydrocarbons taken out is removed by a filter F2 in a filtering apparatus D6. In the present embodiment, a time for replacing or washing the filter F2 is determined based on a result of Step S10.

Hereinafter, each of Step S1 to S11 will be described in more detail.

(Step S1)

In Step S1, first, a sulfur compound contained in natural gas is removed by a desulfurization apparatus (not shown). Usually, the desulfurization apparatus is configured by a hydrogenation desulfurization reactor packed with a known hydrogenation desulfurization catalyst and an adsorptive desulfurization apparatus provided at the following stage thereof and packed with an adsorptive material for hydrogen sulfide such as zinc oxide. The natural gas is fed to the hydrogenation desulfurization reactor with hydrogen, and the sulfur compound in the natural gas is converted into hydrogen sulfide. Subsequently, in the adsorptive desulfurization apparatus, the hydrogen sulfide is removed by adsorption, and the natural gas is desulfurized. By the desulfurization of the natural gas, poisoning of a reforming catalyst packed in the reformer, the FT synthesis catalyst to be used in Step S2, and the like by the sulfur compound is prevented.

The desulfurized natural gas is subjected to reforming using carbon dioxide and steam in the reformer to produce synthesis gas at a high temperature containing carbon monoxide gas and hydrogen gas as main components. The reforming reaction of the natural gas in Step S1 is represented by the following chemical reaction formulae (1) and (2). It is to be noted that the reforming method is not limited to a steam/carbon dioxide gas reforming method using carbon dioxide and steam; for example, a steam reforming method, a partial oxidation reforming method (PDX) using oxygen, an autothermal reforming method (AIR) that is a combination of the partial oxidation reforming method and the steam reforming method, a carbon dioxide gas reforming method, or the like can be also used.

$$CH_4 + H_2O \rightarrow CO + 3H_2 \quad (1)$$

$$CH_4 + CO_2 \rightarrow 2CO + 2H_2 \quad (2)$$

(Step S2)

In Step S2, the synthesis gas produced in Step S1 is fed to the slurry bubble column reactor C2, and hydrocarbons are synthesized from hydrogen gas and carbon monoxide gas in the synthesis gas.

A slurry bubble column FT reaction system including the slurry bubble column reactor C2 mainly includes the slurry bubble column reactor C2 that accommodates a slurry containing the FT synthesis catalyst, a gas feeder (not shown) that blows the synthesis gas into a bottom portion of the reactor, a line L2 that takes out the light hydrocarbons which are obtained by the FT synthesis reaction and are gaseous under the condition within the reactor, and the unreacted synthesis gas from a top of the slurry bubble column reactor C2, a gas liquid separator D2 that cools the light hydrocarbons and the unreacted synthesis gas taken out from the line L2, and separates a condensed part of the light hydrocarbons and a gaseous content into gas and liquid, and a effluent pipe L6 that takes out the slurry containing the hydrocarbons including a wax (heavy liquid hydrocarbons) and the FT synthesis catalyst from the reactor, for example. Moreover, inside of the slurry bubble column reactor C2, a heat conducting pipe (not shown) for removing reaction heat generated by the FT synthesis reaction, through which cool water is flowed, is provided.

As the FT synthesis catalyst used in the slurry bubble column reactor C2, a known supported type FT synthesis catalyst in which an active metal is supported by an inorganic oxide catalyst support is used. As the inorganic oxide catalyst support, porous oxides such as silica, alumina, titania, magnesia, and zirconia are used; silica or alumina is preferable, and silica is more preferable. Examples of the active metal include cobalt, ruthenium, iron, and nickel; cobalt and/or ruthenium is preferable, and cobalt is more preferable. The amount of the active metal to be supported is preferably 3 to 50% by mass and more preferably 10 to 40% by mass based on the mass of the catalyst support. In the case where the amount of the active metal to be supported is less than 3% by mass, the activity tends to be insufficient; and in the case where the amount of the active metal to be supported is more than 50% by mass, the activity tends to be reduced by aggregation of the active metal. Further, in addition to the above-described active metal, other components may be supported in the FT synthesis catalyst for the purpose of improving the activity or controlling a carbon number of hydrocarbons to be produced and a distribution thereof. Examples of the other component include a compound containing a metal element such as zirconium, titanium, hafnium, sodium, lithium, and magnesium. It is preferable that the average particle size of the FT synthesis catalyst particles be 40 to 150 μm so that the catalyst particles may easily flow within the slurry bed reactor as a slurry suspended in the liquid hydrocarbons. It is also preferable that, from the viewpoint of the fluidity as the slurry, the shape of the FT synthesis catalyst particles be spherical.

The active metal is supported by a catalyst support by a known method. Examples of a compound containing the active metal element used upon supporting can include salts of mineral acid of an active metal, such as nitric acid salts, hydrochloric acid salts, and sulfuric acid salts; salts of organic acid such as formic acid, acetic acid, and propionic acid; and complex compounds such as acetylacetonate complexes. A supporting method is not particularly limited, but an impregnation method represented by an Incipient Wetness method using a solution of a compound containing an active metal element is preferably adopted. The catalyst support by which the compound containing an active metal element is supported is dried by a known method, and more preferably calcined under an air atmosphere by a known method. A calcination temperature is not particularly limited, and generally about 300 to 600° C. By calcination, the compound containing an active metal element on the catalyst support is converted into metal oxide.

In order to allow the FT synthesis catalyst to exert high activity to the FT synthesis reaction, it is necessary that the active metal atom be converted into a metal by reduction of the catalyst in which the active metal atom is oxidized. The reduction is usually performed by bringing the catalyst in contact with reducing gas under heating. Examples of the reducing gas include hydrogen gas, gas containing hydrogen gas, such as mixed gas of hydrogen gas and inert gas such as nitrogen gas, and carbon monoxide gas; preferable is hydrogen containing gas, and more preferable is hydrogen gas. A temperature in the reduction is not particularly limited, but it is preferably generally 200 to 550° C. In the case where the reduction temperature is lower than 200° C., the active metal atom tends not to be sufficiently reduced and not to sufficiently exert the catalyst activity; and in the case where the temperature is higher than 550° C., the catalyst activity tends to be reduced due to aggregation of the active metal or the like. A pressure in the reduction is not particularly limited, but it is preferably generally 0.1 to 10 MPa. In the case where the pressure is lower than 0.1 MPa, the active metal atom tends not to be sufficiently reduced and not to sufficiently exert the catalyst activity; and in the case where the pressure is higher than 10 MPa, facility cost tends to be increased for a need to increase pressure resistance of the apparatus. A time for the reduction is not particularly limited, but it is preferably generally 0.5 to 50 hours. In the case where the reduction time is less than 0.5 hours, the active metal atom tends not to be sufficiently reduced and not to sufficiently exert the catalyst activity; and in the case where the reduction time is more than 50 hours, the catalyst activity tends to be reduced due to aggregation of the active metal or the like, and the efficiency tends to be reduced. A facility in which the reduction is performed is not particularly limited, but, for example, the reduction may be performed in the absence of the liquid hydrocarbons within the reactor that performs the FT synthesis reaction. Moreover, the reduction may be performed within a facility connected to the reactor that performs the FT synthesis reaction, and the catalyst may be transferred through a piping to the reactor that performs the FT synthesis, without being contact with the air.

On the other hand, in the case where the reduction is performed in a facility located in a place different from that of the facility that performs the FT synthesis reaction such as a catalyst production facility, the catalyst activated by the reduction is deactivated if the catalyst is brought into contact with the air during transportation or the like. In order to prevent this, the activated catalyst is subjected to a stabilization treatment to prevent deactivation caused by contact with the air. Examples of the stabilization treatment include a method for subjecting an activated catalyst to a light oxidation treatment to form an oxidation coating on a surface of an active metal so that oxidation due to contact with the air does not further proceed, or a method for coating an activated catalyst with a hydrocarbon wax or the like without being contact with the air to block contact with the air. In the method for forming an oxidation coating, the catalyst can be subjected to the FT synthesis reaction as it is after transportation; and also in the method for performing covering with wax or the like, when the catalyst is suspended in liquid hydrocarbons to form a slurry, the wax or the like used for covering is dissolved in the liquid hydrocarbons, and the activity is exerted.

A reaction condition on the FT synthesis reaction in the slurry bubble column reactor C2 is not limited, but, for example, the following reaction condition is selected. Namely, it is preferable that a reaction temperature be 150 to 300° C. from the viewpoint of increase in the conversion rate of carbon monoxide and a carbon number of hydrocarbons to be produced. It is preferable that a reaction pressure be 0.5 to 5.0 MPa. It is preferable that a ratio (molar ratio) of hydrogen/carbon monoxide in raw material gas be 0.5 to 4.0. Here, it is desirable that the conversion rate of carbon monoxide be not less than 50% from the viewpoint of the production efficiency of the FT synthetic oil.

Inside of the slurry bubble column reactor C2, a slurry in which the FT synthesis catalyst particles are suspended in the liquid hydrocarbons (product of the FT synthesis reaction) is accommodated. The synthesis gas (CO and $H_2$) obtained in Step S1 is injected into the slurry within the reactor through a dispersion plate installed in the bottom portion of the slurry bubble column reactor C2. The synthesis gas blown into the slurry turns to bubbles, which move upward in the slurry to the upper portion of the slurry bubble column reactor C2. In the course thereof, the synthesis gas is dissolved in the liquid hydrocarbons to be contact with the FT synthesis catalyst particles, thereby, the FT synthesis reaction proceeds to produce hydrocarbons. The FT synthesis reaction is represented by the following chemical reaction equation (3), for example.

$$2nH_2 + nCO \rightarrow (-CH_2-)_n + nH_2O \quad (3)$$

A gaseous phase portion exists in the upper portion of the slurry accommodated in the slurry bubble column reactor C2. The light hydrocarbons which are produced by the FT synthesis reaction and are gaseous under the condition within the slurry bubble column reactor C2 and the unreacted synthesis gas (CO and $H_2$) move from a slurry phase to this gaseous phase portion, and are further taken out from the top portion of the slurry bubble column reactor C2 through the line L2.

The slurry containing the hydrocarbons (heavy liquid hydrocarbons) which are produced by the FT synthesis reaction and are in a liquid state under the condition within the slurry bubble column reactor C2 and the FT synthesis catalyst particles is fed from the central portion of the slurry bubble column reactor C2 through the line L6 to the catalyst separator D4.

As the product of the FT synthesis reaction, hydrocarbons (light hydrocarbons) which are gaseous under the condition within the slurry bubble column reactor C2 and hydrocarbons (heavy hydrocarbon oil) which are in a liquid state under the condition within the slurry bubble column reactor C2 are obtained. These hydrocarbons are substantially normal paraffins, and few aromatic hydrocarbons, naphthene hydrocarbons and isoparaffins are contained. Distribution of a carbon number of the light hydrocarbons and heavy hydrocarbon oil in total widely ranges from $C_4$ or less as gas at normal temperature to approximately $C_{80}$, for example, as a solid (wax) at room temperature. The product of the FT synthesis reaction also contains olefins and oxygen-containing compounds containing oxygen atoms derived from carbon monoxide (e.g., alcohols) as by-products.

(Step S3)

In Step S3, the heavy liquid hydrocarbons are taken out by a separation system provided outside of the reactor C2, and fed to the following stage. The system mainly includes the catalyst separator D4 that separates the slurry taken out via the effluent pipe L6 to the heavy liquid hydrocarbons and the FT synthesis catalyst particles, and the sending-back pipe L10 that sends back the FT synthesis catalyst particles separated by the catalyst separator D4 and a part of the hydrocarbon oil to the reactor C2.

The FT synthesis catalyst particles in the slurry are captured in the filter F1 provided within the catalyst separator D4. The heavy liquid hydrocarbons in the slurry pass through the filter to be separated from the FT synthesis catalyst particles and to be taken out by a line L8. The heavy liquid hydrocarbons are heated in a heat exchanger H2 provided on the line L8 and then fed to the first fractionator C4.

As a composition of the heavy liquid hydrocarbons, normal paraffins with carbon number of 20 or more and about 100 or less is a main component.

As long as the opening of the filter F1 provided in the catalyst separator D4 is less than the particle size of the FT synthesis catalyst particle, the size of the opening is not particularly limited, but it is preferably 10 to 20 μm and more preferably 10 to 15 μm. The FT synthesis catalyst particles captured by the filter provided in the catalyst separator D4 are returned through the line L10 to the slurry bubble column reactor C2 by properly flowing liquid hydrocarbons in a direction opposite to the ordinary flow direction (backwashing), and reused.

A part of the FT synthesis catalyst particles that flow as the slurry in the slurry bubble column reactor C2 wears or collapses due to friction between the catalyst particles, friction with the wall of the apparatus or the heat conducting pipe provided within the reactor for cooling, or damage or the like caused by the reaction heat, thereby to produce catalyst particulates. If the catalyst particulates are contained in the slurry in a large amount, clogging of the filter tends to be generated, but the particulate content can be estimated in Step S9 in the present embodiment, and the backwashing in Step S10 is preformed based on this result.

On the other hand, the light hydrocarbons and the unreacted synthesis gas taken out from the gaseous phase portion of the slurry bubble column reactor C2 are separated by the gas liquid separator D2 including a cooler (not shown) connected to the line L2 into a gas fraction containing the unreacted synthesis gas and hydrocarbon gas having $C_4$ or less as main components and liquid hydrocarbons (light liquid hydrocarbons) condensed by cooling. Of these, the gas fraction is recycled to the slurry bubble column reactor C2, and the unreacted synthesis gas contained in the gas fraction is subjected to the FT synthesis reaction again. On the other hand, the light liquid hydrocarbons pass through the line L4, mix with the heavy liquid hydrocarbons fed from the catalyst separator D4 in a line L8, and are fed to the first fractionator C4.

(Step S4)

In Step S4, a mixture of the heavy liquid hydrocarbons fed from the catalyst separator D4 and the light liquid hydrocarbons fed from the gas liquid separator D2 is fractionated in the first fractionator C4. By the fractionation, the FT synthetic oil is separated to a raw naphtha fraction having approximately $C_5$ to $C_{10}$, with a boiling point of lower than 150° C., a raw middle distillate having approximately $C_{11}$ to $C_{21}$, with a boiling point of about 150 to 360° C., and a raw wax fraction having approximately not less than $C_{22}$, with a boiling point of higher than about 360° C.

The raw naphtha fraction is taken out through a line L14 connected to a top of the first fractionator, and the raw middle distillate is taken out through a line L18 connected to a central portion of the first fractionator 40. The raw wax fraction is taken out through a line L12 connected to a bottom portion of the first fractionator C4.

(Step S5)

The raw wax fraction transferred from the first fractionator C4 in Step S4 is heated, with hydrogen gas fed by a feed line (not shown) for hydrogen gas connected to the line L12, to a temperature necessary for hydrocracking of the raw wax fraction by a heat exchanger H4 provided on the line L12, and then fed to the hydrocracking apparatus C6 to be hydrocracked. The raw wax fraction not sufficiently hydrocracked in the hydrocracking apparatus C6 (hereinafter, optionally referred to as the "uncracked wax fraction") is recovered as a bottom oil of the second fractionator C12 in Step S8, recycled by a line L38 to the line L12, and fed to the hydrocracking apparatus C6 again.

The type of the hydrocracking apparatus C6 is not particularly limited, and a fixed bed flow reactor packed with a hydrocracking catalyst is preferably used. The reactor may be singular, or a plurality of reactors may be provided in serial or in parallel. Moreover, the catalyst bed within the reactor may be singular or plural.

As the hydrocracking catalyst packed in the hydrocracking apparatus C6, a known hydrocracking catalyst is used, and a catalyst in which a metal that is an element having hydrogenation activity and belongs to Group 8 to Group 10 in the periodic table is supported by an inorganic catalyst support having solid acidity is preferably used.

Examples of the inorganic catalyst support that constitutes the hydrocracking catalyst and has suitable solid acidity include those constituted from zeolites such as ultrastable Y-type (USY) zeolite, Y-type zeolite, mordenite, and β zeolite, and one or more inorganic compounds selected from amorphous composite metal oxides having heat resistance such as silica alumina, silica zirconia, and alumina boria. Further, as the catalyst support, compositions constituted by comprising USY zeolite, and one or more amorphous composite metal oxides selected from silica alumina, alumina boria, and silica zirconia are more preferable, and compositions constituted by comprising USY zeolite and alumina boria and/or silica alumina are still more preferable.

USY zeolite is one obtained by ultra-stabilizing Y-type zeolite by a hydrothermal treatment and/or an acid treatment; in addition to a fine porous structure called micro pores that Y-type zeolite originally has and whose pore size is not larger than 2 nm, new pores having a pore size in the range of 2 to 10 nm are formed. The average particle size of USY zeolite is not particularly limited, but it is preferably not larger than 1.0 μm, and more preferably not larger than 0.5 μm. Moreover, in USY zeolite, it is preferable that a molar ratio of silica/alumina (molar ratio of silica to alumina) be 10 to 200, it is more preferable that the molar ratio be 15 to 100, and it is still more preferable that the molar ratio be 20 to 60.

Moreover, it is preferable that the catalyst support contain 0.1 to 80% by mass of a crystalline zeolite and 0.1 to 60% by mass of an amorphous composite metal oxide having heat resistance.

The catalyst support can be produced as follows: a catalyst support comprising the inorganic compound having solid acidity and a binder is molded, and calcined. A proportion of the inorganic compound having solid acidity to be compounded is preferably 1 to 70% by mass, and more preferably 2 to 60% by mass based on the entire mass of the catalyst support. Moreover, in the case where the catalyst support contains USY zeolite, a proportion of USY zeolite to be compounded is preferably 0.1 to 10% by mass, and more preferably 0.5 to 5% by mass based on the entire mass of the catalyst support. Further, in the case where the catalyst support contains USY zeolite and alumina boria, it is preferable that a proportion of USY zeolite to alumina boria to be compounded (USY zeolite/alumina boria) be 0.03 to 1 in the mass ratio. Moreover, in the case where the catalyst support contains USY zeolite and silica alumina, it is preferable that a proportion of USY zeolite to silica alumina to be compounded (USY zeolite/silica alumina) be 0.03 to 1 in the mass ratio.

The binder is not particularly limited, but alumina, silica, titania, and magnesia are preferable, and alumina is more preferable. An amount of the binder to be compounded is preferably 20 to 98% by mass and more preferably 30 to 96% by mass based on the entire mass of the catalyst support.

A temperature in calcining the catalyst support is preferably in the range of 400 to 550° C., more preferably in the range of 470 to 530° C., and still more preferably in the range of 490 to 530° C. Calcination at such a temperature can give sufficient solid acidity and mechanical strength to the catalyst support.

Examples of Groups 8 to 10 metals in the periodic table supported by the catalyst support and having hydrogenation activity specifically include cobalt, nickel, rhodium, palladium, iridium, and platinum. Among them, metals selected from nickel, palladium, and platinum are preferably used singularly or in combinations of two or more. These metals can be supported on the catalyst support mentioned above by a standard method such as impregnation and ion exchange. An amount of the metal to be supported is not particularly limited, but it is preferable that the entire amount of the metal be 0.1 to 3.0% by mass based on the mass of the catalyst support. Here, the periodic table of the elements refers to the long form of the periodic table of the elements based on the specification by IUPAC (the International Union of Pure and Applied Chemistry).

In the hydrocracking apparatus C6, while the raw wax fraction and a part of the uncracked wax fraction (hydrocarbons having approximately $C_{21}$ or more) are converted into hydrocarbons having approximately $C_{20}$ or less by hydrocracking, further, a part thereof is converted into a naphtha fraction (approximately $C_5$ to $C_{10}$) lighter than the target middle distillate (approximately $C_{11}$ to $C_{20}$) and further gaseous hydrocarbons having $C_4$ or less by excessive cracking. On the other hand, the raw wax fraction and a part of the uncracked wax fraction do not undergo hydrocracking sufficiently, and turn to an uncracked wax fraction having approximately $C_{21}$ or more. The composition of the hydrocracking product is determined according to the hydrocracking catalyst to be used and the hydrocracking reaction condition. Here, the "hydrocracking product" refers to all hydrocracking products containing the uncracked wax fraction, unless otherwise specified. If the hydrocracking reaction condition is tighter than necessary, the content of the uncracked wax fraction in the hydrocracking product is reduced while a light fraction equal to or lighter than the naphtha fraction is increased to reduce the yield of the target middle distillate. On the other hand, if the hydrocracking reaction condition is milder than necessary, the uncracked wax fraction is increased to reduce the yield of the middle distillate. In the case where a ratio M2/M1 of a mass M2 of the cracking product with a boiling point of 25 to 360° C. to a mass M1 of all cracking products with a boiling point of 25° C. or higher is defined as a "cracking rate," the reaction condition is selected so that the cracking ratio M2/M1 may be usually 20 to 90%, preferably 30 to 80%, and more preferably 45 to 70%.

In the hydrocracking apparatus C6, in parallel with the hydrocracking reaction, a hydro-isomerization reaction of normal paraffins that constitute the raw wax fraction and the uncracked wax fraction or the hydrocracking products thereof proceeds to produce isoparaffins. In the case where the hydrocracking product is used as a base stock for fuel oil, isoparaffins to be produced by the hydro-isomerization reaction is a component that contributes to improvement in cold flow property (fluidity in a low temperature), and it is preferable that the production rate be high. Further, removal of olefins and oxygen-containing compounds such as alcohols that are by-products of the FT synthesis reaction contained in the raw wax fraction also proceeds. Namely, the olefins are converted into paraffin hydrocarbons by hydrogenation, and the oxygen-containing compounds are converted into paraffin hydrocarbons and water by hydrogenation deoxidation.

The reaction condition in the hydrocracking apparatus C6 is not limited, but the following reaction condition can be selected. Namely, examples of a reaction temperature include 180 to 400° C., 200 to 370° C. is preferable, 250 to 350° C. is more preferable, and 280 to 350° C. is particularly preferable. If the reaction temperature is higher than 400° C., not only cracking into the light fraction tends to proceed to reduce the yield of the middle distillate, but also the product tends to be colored and to be restricted to use as the base stock for fuel oil. On the other hand, if the reaction temperature is lower than 180° C., not only the hydrocracking reaction tends not to proceed sufficiently and the yield of the middle distillate tends to be reduced, but also production of isoparaffins by the hydro-isomerization reaction tends to be suppressed and oxygen-containing compounds such as alcohols tend not to sufficiently be removed to remain. Examples of a hydrogen partial pressure include 0.5 to 12 MPa, and 1.0 to 5.0 MPa is preferable. If the hydrogen partial pressure is lower than 0.5 MPa, hydrocracking and hydro-isomerization tend not to sufficiently proceed, on the other hand, if the hydrogen partial pressure is higher than 12 MPa, high pressure resistance is demanded for the apparatus, and facility cost tends to be increased. Examples of a liquid hourly space velocity (LHSV) of the raw wax fraction and the uncracked wax fraction include 0.1 to 10.0 $h^{-1}$, and 0.3 to 3.5 $h^{-1}$ is preferable. If the LHSV is lower than 0.1 $h^{-1}$, hydrocracking tends to excessively proceed and productivity tends to be reduced, on the other hand, if the LHSV is higher than 10.0 $h^{-1}$, hydrocracking and hydro-isomerization tend not to sufficiently proceed. Examples of a ratio of hydrogen/oil include 50 to 1000 NL/L, and 70 to 800 NL/L is preferable. If the ratio of hydrogen/oil is lower than 50 NL/L, hydrocracking and hydro-isomerization tend not to sufficiently proceed, on the other hand, if the ratio of hydrogen/oil is higher than 1000 NL/L, a large-sized hydrogen feeding apparatus and the like tend to be needed.

In this example, the hydrocracking product and unreacted hydrogen gas flowed from the hydrocracking apparatus C6 are cooled, and separated into gas and liquid at two stages by a gas liquid separator D8 and a gas liquid separator D10, relatively heavy liquid hydrocarbons containing the uncracked wax fraction is obtained from the gas liquid separator D8, and a gas fraction mainly containing hydrogen gas and gaseous hydrocarbons having $C_4$ or less and relatively light liquid hydrocarbons are obtained from the gas liquid separator D10. By such two-stage cooling and gas liquid separation, clogging of the line accompanied by solidification by rapid cooling of the uncracked wax fraction contained in the hydrocracking product can be prevented from occurring. The liquid hydrocarbons each obtained in the gas liquid separator D8 and the gas liquid separator D10 mix with a line L32 through a line L28 and a line L26, respectively. A gaseous content mainly containing hydrogen gas and gaseous hydrocarbons with $C_4$ or less separated in a gas liquid separator D12 is fed to the middle distillate hydrotreating apparatus C8 and the naphtha fraction hydrotreating apparatus C10 through a line (not shown) connecting the gas liquid separator D10 to the line L18 and a line L14, and the hydrogen gas is reused.

(Step S6)

The raw middle distillate taken out from the first fractionator C4 by the line L18 is heated, with the hydrogen gas fed by a feed line (not shown) of the hydrogen gas connected to the line L18, to a temperature needed for hydrotreating of the raw middle distillate by a heat exchanger H6 installed in the line L18, and then fed to the middle distillate hydrotreating apparatus C8 to be hydrotreated.

The type of the middle distillate hydrotreating apparatus C8 is not particularly limited, and a fixed bed flow reactor packed with a hydrotreating catalyst is preferably used. The reactor may be singular, or a plurality of reactors may be provided in serial or in parallel. Moreover, the catalyst bed within the reactor may be singular or plural.

As the hydrotreating catalyst used in the middle distillate hydrotreating apparatus C8, catalysts usually used for hydrotreating and/or hydro-isomerization in petroleum refining or the like, namely, the catalysts in which a metal having hydrogenation activity is supported by an inorganic catalyst support can be used.

As the metal having hydrogenation activity that constitutes the hydrotreating catalyst, one or more metals selected from the group consisting of metals in Groups 6, 8, 9, and 10 in the periodic table of the elements are used. Specific examples of these metals include noble metals such as platinum, palladium, rhodium, ruthenium, iridium, and osmium, or cobalt, nickel, molybdenum, tungsten, and iron; preferable are platinum, palladium, nickel, cobalt, molybdenum, and tungsten, and more preferable are platinum and palladium. Moreover, a plurality of these metals are also preferably used in combination; examples of a preferable combination in this case include platinum-palladium, cobalt-molybdenum, nickel-molybdenum, nickel-cobalt-molybdenum, and nickel-tungsten.

Examples of the inorganic catalyst support that constitutes the hydrotreating catalyst include metal oxides such as alumina, silica, titania, zirconia, and boria. These metal oxides may be used singularly, or used as a mixture of two or more thereof, or a composite metal oxide such as silica alumina, silica zirconia, alumina zirconia, and alumina boria. From the viewpoint of efficiently proceeding hydro-isomerization of normal paraffins at the same time with hydrotreating, it is preferable that the inorganic catalyst support be a composite metal oxide having solid acidity such as silica alumina, silica zirconia, alumina zirconia, and alumina boria. Moreover, a small amount of zeolite may be contained in the inorganic catalyst support. Further, in order to enhance the moldability and mechanical strength of the catalyst support, a binder may be compounded in the inorganic catalyst support. Examples of a preferable binder include alumina, silica, and magnesia.

In the case where the metal is the above-described noble metal, it is preferable that a content of the metal having hydrogenation activity in the hydrotreating catalyst be approximately 0.1 to 3% by mass as a metal atom based on the mass of the catalyst support. Moreover, in the case where the metal is a metal other than the above-described noble metal, it is preferable that the content be approximately 2 to 50% by mass as a metal oxide based on the mass of the catalyst support. In the case where the content of the metal having hydrogenation activity is less than the lower limit value, hydrotreating and hydro-isomerization tend not to sufficiently proceed. On the other hand, in the case where the content of the metal having hydrogenation activity is more than the upper limit value, dispersion of the metal having hydrogenation activity tends to be reduced to reduce the activity of the catalyst, and cost of the catalyst is increased.

In the middle distillate hydrotreating apparatus C8, the raw middle distillate (which contains normal paraffins with approximately $C_{11}$ to $C_{20}$ as a main component) is hydrotreated. In this hydrotreating, olefins that are a by-product of the FT synthesis reaction contained in the raw middle distillate are hydrogenated to be converted into paraffin hydrocarbons. Moreover, oxygen-containing compounds such as alcohols are converted into paraffin hydrocarbons and water by a hydrogenation deoxidation reaction. Moreover, in parallel with the hydrotreating, the hydro-isomerization reaction of normal paraffins that constitute the raw middle distillate proceeds to produce isoparaffins In the case where the middle distillate is used as the base stock for fuel oil, the isoparaffins produced by the hydro-isomerization reaction are a component contributing to improvement in cold flow property, and it is preferable that the production rate be high.

The reaction condition in the middle distillate hydrogen refining reactor C8 is not limited, but the following reaction condition can be selected. Namely, examples of a reaction temperature include 180 to 400° C., 200 to 370° C. is preferable, 250 to 350° C. is more preferable, and 280 to 350° C. is particularly preferable. If the reaction temperature is higher than 400° C., not only cracking into the light fraction tends to proceed to reduce the yield of the middle distillate, but also the product tends to be colored and to be restricted to use as the base stock for fuel oil. On the other hand, if the reaction temperature is lower than 180° C., oxygen-containing compounds such as alcohols tend not to sufficiently be removed to remain, and production of isoparaffins by the hydro-isomerization reaction tends to be suppressed. Examples of a hydrogen partial pressure include 0.5 to 12 MPa, and 1.0 to 5.0 MPa is preferable. If the hydrogen partial pressure is lower than 0.5 MPa, hydrotreating and hydro-isomerization tend not to sufficiently proceed, on the other hand, if the hydrogen partial pressure is higher than 12 MPa, high pressure resistance is demanded for the apparatus, and facility cost tends to be increased. Examples of a liquid hourly space velocity (LHSV) of the raw middle distillate include 0.1 to 10.0 $h^{-1}$, and 0.3 to 3.5 $h^{-1}$ is preferable. If the LHSV is lower than 0.1 $h^{-1}$, cracking into the light fraction tends to proceed to reduce the yield of the middle distillate, and productivity tends to be reduced, on the other hand, if the LHSV is higher than 10.0 $h^{-1}$, hydrotreating and hydro-isomerization tend not to sufficiently proceed. Examples of a ratio of hydrogen/oil include 50 to 1000 NL/L, and 70 to 800 NL/L is preferable. If the ratio of hydrogen/oil is lower than 50 NL/L, hydrotreating and hydro-isomerization tend not to sufficiently proceed, on the other hand, if the ratio of hydrogen/oil is higher than 1000 NL/L, a large-sized hydrogen feeding apparatus and the like tend to be needed.

A effluent oil from the middle distillate hydrotreating reactor C8, from which a gas fraction mainly containing unreacted hydrogen gas has been separated in the gas liquid separator D12 connected to the line L30, is transferred through the line L32, and mixes with the hydrocracking product of the liquid wax fraction transferred by the line L26. The gas fraction mainly containing hydrogen gas separated in the gas liquid separator D12 is fed to the hydrocracking apparatus C6, and reused.

(Step S7)

The raw naphtha fraction taken out from the top of the first fractionator C4 by the line L14 is heated, with the hydrogen gas fed by a feed line (not shown) of the hydrogen gas connected to the line L14, to a temperature needed for hydrotreating of the raw naphtha fraction by a heat exchanger H8 installed in the line L14, and then fed to the naphtha fraction hydrotreating apparatus C10 to be hydrotreated.

The type of the naphtha fraction hydrotreating apparatus 10 is not particularly limited, and a fixed bed flow reactor packed with a hydrotreating catalyst is preferably used. The reactor may be singular, or a plurality of reactors may be provided in serial or in parallel. Moreover, the catalyst bed within the reactor may be singular or plural.

The hydrotreating catalyst used for the naphtha fraction hydrotreating apparatus 10 is not particularly limited, but the hydrotreating catalyst may be the same hydrotreating catalyst as that used for hydrotreating of the raw middle distillate.

In the naphtha fraction hydrotreating apparatus C10, unsaturated hydrocarbons contained in the raw naphtha fraction (which contains normal paraffins with approximately $C_5$ to $C_{10}$ as a main component) are converted into paraffin hydrocarbons by hydrogenation. Moreover, oxygen-containing compounds contained in the raw naphtha fraction, such as alcohols, are converted into paraffin hydrocarbons and water by hydrogenation deoxidation. It is to be noted that, in the naphtha fraction, the hydro-isomerization reaction does not proceed much because a carbon number is small.

The reaction condition in the naphtha fraction hydrotreating apparatus C10 is not limited, but the same reaction condition as that in the middle distillate hydrotreating apparatus C8 can be selected.

The effluent oil of the naphtha fraction hydrotreating apparatus C10 is fed through a line L34 to a gas liquid separator D14, and in the gas liquid separator D14, the effluent oil is separated into the gas fraction in which hydrogen gas is a main component, and liquid hydrocarbons. The gas fraction obtained by this separation is fed to the hydrocracking apparatus C6, and the hydrogen gas contained in this is reused. On the other hand, the liquid hydrocarbons obtained by this separation are transferred through a line L36 to the naphtha stabilizer C14. Moreover, a part of the liquid hydrocarbons is recycled through a line L48 to the line L14 upstream of the naphtha fraction hydrotreating apparatus C10. Because an amount of heat to be generated in hydrotreating of the raw naphtha fraction (hydrogenation of olefins and hydrogenation deoxidation of alcohols and the like) is large, a part of the liquid hydrocarbons is recycled to the naphtha fraction hydrotreating apparatus C10 and the raw naphtha fraction is diluted, thereby suppressing increase in the temperature in the naphtha fraction hydrotreating apparatus C10.

In the naphtha stabilizer C14, the liquid hydrocarbons fed from the naphtha fraction hydrotreating apparatus C10 and the second fractionator C12 are fractionated to obtain refined naphtha with carbon number of $C_5$ to $C_{10}$ as a product. The refined naphtha is transferred from the bottom of the naphtha stabilizer C14 through a line L46 to a naphtha tank T6, and stored. On the other hand, from a line L50 connected to a top of the naphtha stabilizer C14, hydrocarbon gas in which hydrocarbons with carbon number being a predetermined number or less ($C_4$ or less) are a main component is discharged. Because the hydrocarbon gas is not a target product, the hydrocarbon gas is introduced into an external burning facility (not shown) to be burned, and then discharged into the air.

(Step S8)

A mixed oil comprising the liquid hydrocarbons obtained from the effluent oil from the hydrocracking apparatus C6 and the liquid hydrocarbons obtained from the effluent oil from the middle distillate hydrotreating apparatus C8 is heated by a heat exchanger 1110 provided in the line L32, and then fed to the second fractionator C12 to be fractionated into hydrocarbons having approximately $C_{10}$ or less, a kerosene fraction, a gas oil fraction, and an uncracked wax fraction. The hydrocarbons having approximately $C_{10}$ or less with a boiling point of less than about 150° C. are taken out from a top of the second fractionator C12 by a line L44. The kerosene fraction with a boiling point of about 150 to 250° C. is taken out from a central portion of the second fractionator C12 by a line L42 to be stored in a tank T4. The gas oil fraction with a boiling point of about 250 to 360° C. is taken out from a lower portion of the second fractionator C12 by a line L40 to be stored in a tank T2. The uncracked wax fraction with a boiling point of higher than about 360° C. is taken out from a bottom of the second fractionator C12 to be recycled by the line L38 to the line L12 upstream of the hydrocracking apparatus C6. The hydrocarbons having approximately $C_{10}$ or less taken out from the top of the second fractionator C12 are fed by the lines L44 and L36 to the naphtha stabilizer, and fractionated with the liquid hydrocarbons fed from the naphtha fraction hydrotreating apparatus C10.

(Step S9)

In Step S9, a part of the slurry taken out via the effluent pipe L6 is taken, and a content of particulates having a predetermined particle size or less in the slurry is estimated by the method for estimating a particulate content in a slurry according to the present invention. This step can be performed periodically and/or as needed.

The method for estimating a particulate content in a slurry according to the present invention is characterized by comprising, based on a correlation between a visible light transmittance and a content of solid particles having a predetermined particle size or less at a temperature at which hydrocarbons including a wax are liquefied when the solid particles having the predetermined particle size or less are dispersed in the hydrocarbons, estimating a content of particulates having a predetermined particle size or less in the slurry from a visible light transmittance of a supernatant part when the slurry is left to stand at the temperature.

In the present embodiment, a calibration curve by a standard sample is preliminarily prepared as the correlation, and this calibration curve can be used to estimate a content of particulates having a predetermined particle size or less in the slurry.

As a procedure for preparing the calibration curve, for example, first, an unused FT synthesis catalyst is ground and ground products are further sieved, thereby preparing catalyst particulates having a predetermined particle size or less. Examples of a grinding method include a ball mill and a jet mill. Examples of a method for sieving a ground product include a dry vibration sieve.

Then, the catalyst particulates obtained as described above are mixed with hydrocarbons including a wax, thereby preparing standard samples each having a different particulate content. Then, the catalyst particulates are dispersed with stirring while being heated to a temperature at which the hydrocarbons are liquefied, and each standard sample is charged in a vessel for measuring a visible light transmittance. Then, this vessel is left to stand under a temperature at which the hydrocarbons are liquefied, and thereafter the visible light transmittance is measured. It is to be noted that the visible light transmittance is measured at a position where the catalyst particulates having a predetermined particle size are not sedimented, and a time for being left to stand is set so as to satisfy this.

Figure 2:
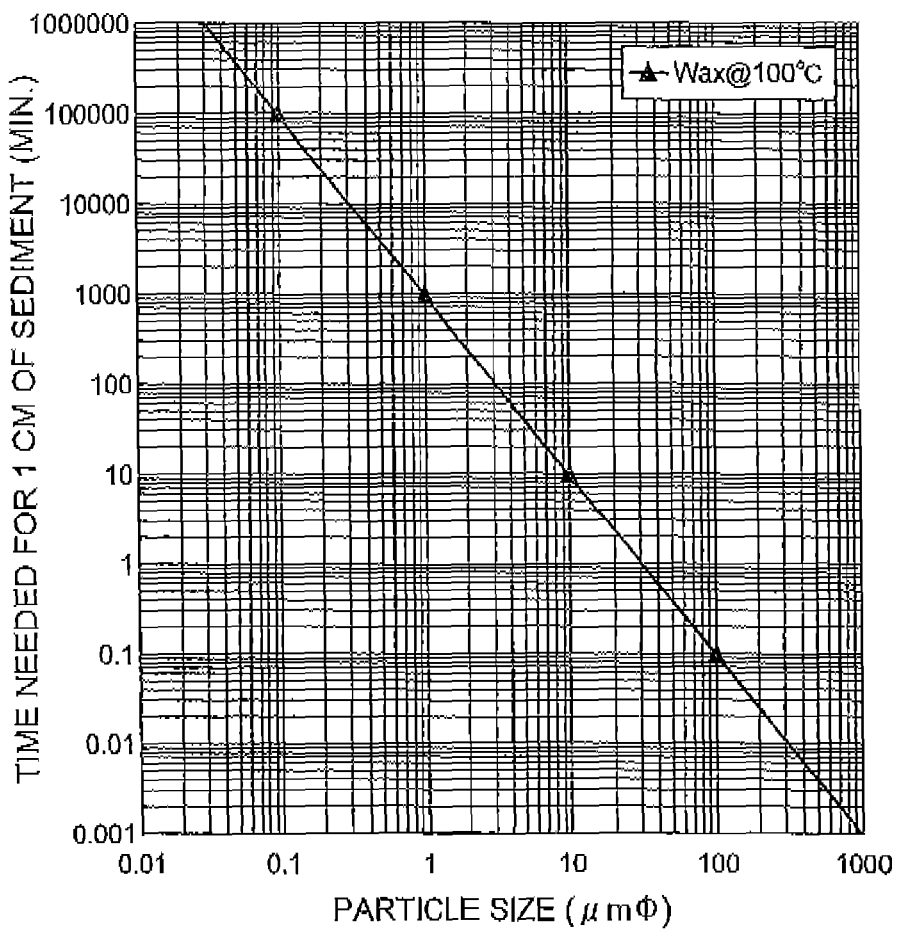
FIG. 2 is a graph showing a relationship between a particle size of catalyst particles dispersed in hydrocarbons including a wax and a time needed for 1 cm of sediment at 100° C.

For this setting, for example, a relationship between a particle size of solid particles dispersed in the hydrocarbons including a wax and a time needed until the solid particles are sedimented by a predetermined distance at a temperature at which the hydrocarbons are liquefied can be used. FIG. 2 is a graph showing a relationship between a particle size of catalyst particles dispersed in hydrocarbons including a wax and a time needed for 1 cm of sediment at 100° C. This graph shows that a time needed for sedimenting catalyst particles having a particle size of 10 μm by 1 cm is 10 minutes, for example. If a standard sample for estimating a catalyst particle content having a particle size of 10 μm or less is measured at a position which is 1 cm deeper than a liquid level, it is preferable that a time for being left to stand be within 10 minutes.

It is to be noted that FIG. 2 is prepared by measuring a viscosity of the hydrocarbons including a wax at 100° C., and using this viscosity and a density value of the catalyst particles to calculate a time needed for sedimenting particles having each particle size in the hydrocarbons at 100° C. by 1 cm with a Stokes equation.

The visible light transmittance can be measured using a quartz glass cell by a Visible/UV light spectrometric analysis apparatus V-660 manufactured by JASCO Corporation.

A wavelength in measuring the visible light transmittance preferably ranges from 500 to 800 nm from the viewpoint of preventing absorption by impurities in the hydrocarbons including a wax.

On the other hand, in a case of measuring the visible light transmittance of the slurry as a subject, the catalyst particles are sufficiently dispersed with stirring while being heated to a temperature at which the hydrocarbons contained in the slurry are liquefied, and the slurry is charged in a vessel (cell) for measuring the visible light transmittance. Then, this vessel is left to stand under the temperature at which the hydrocarbons are liquefied to generate a supernatant part, and thereafter the visible light transmittance of the supernatant part is measured. The FT synthesis catalyst is darkish grey; if the catalyst particles are suspended (or dispersed) in a hydrocarbon medium, this suspension (or dispersion) displays grey and has a lower transmittance at visible light, but it is left to stand under the temperature at which the hydrocarbons are liquefied, thereby making it possible to generate a supernatant part. The time for being left to stand in this case is set so that the supernatant part to be measured does not contain catalyst particles exceeding a predetermined particle size.

For example, with respect to an example shown in FIG. 2, when 10 minutes have elapsed after starting to be left to stand, no particles having a particle size of larger than 10 μm are present at a position which is 1 cm deeper than a liquid level of the slurry, and only particles having a particle size of 10 μm or less are present at the position. The slurry is taken in a cell to be used in a spectrometer and held at 100° C. to be left to stand for 10 minutes, a visible light transmittance of a region in which the particles having a particle size of larger than 10 μm disappear with being sedimented is measured, and consequently the value corresponds to a concentration of particulates which remain in the region and have a particle size of 10 μm or less.

In the present embodiment, it is preferable that the conditions used for measuring the visible light transmittance in preparing the calibration curve (cell, temperature, time for being left to stand, measurement position and the like) be the same as the conditions upon measuring the visible light transmittance of the slurry as a subject. Specifically, the cell, temperature and measurement position are fixed, and the visible light transmittance may be measured over time or may be measured after a predetermined time for being left to stand.

In the foregoing, the example in the case of setting a predetermined particle size to 10 μm is shown, but the present invention is not limited to this example, and an arbitrary particle size can be set as the upper value. Also in this case, it is possible to estimate a content of particulates having an arbitrary particle size or less as in the same manner described above.

A temperature when the sample is left to stand and the visible light transmittance is measured is not particularly limited as long as the temperature is a temperature at which the hydrocarbon medium is liquefied, but the temperature is preferably 100 to 120° C. from the viewpoints of keeping the fluidity of the hydrocarbon medium and preventing the medium from volatilizing, which is a temperature sufficiently below the boiling point of the hydrocarbon medium under atmospheric pressure and can be stably controlled by a temperature regulator accompanied in the spectrometer (V-660 apparatus) to be used in the measurement.

(Step S10)

In Step S10, liquid hydrocarbons stored in a backwashing liquid tank (not shown) are flowed by a pump or the like (not shown) to the filter F1 in the catalyst separator D4 in a direction opposite to the flowing direction. Then, catalyst particles accumulated on the filter are returned into a slurry bed in the reactor C2 via the sending-back pipe L10 with the liquid hydrocarbons as a backwashing liquid.

In the present embodiment, a frequency of performing Step S10 can be determined based on a result of Step S9. For example, the variation in content of catalyst particulates having a predetermined particle size or less in a slurry is monitored by taking the slurry periodically and/or as needed, and Step S10 is performed at the time when the content exceeds, for example, 100 ppm by mass. Thus, clogging of the filter can be prevented while avoiding damage of the filter due to excessive washing of the filter and a decrease in production efficiency.

In the present embodiment, it is preferable that the predetermined particle size be set to that of the opening of the filter F1 from the viewpoint that a particle size considerably contributes to the clogging of the opening.

EXAMPLES

Hereinafter, the present invention will be more specifically described by Examples, but it is not to be limited to the following Examples.

[Preparation of Standard Sample]

An unused FT synthesis catalyst (catalyst with cobalt oxide being supported by a silica catalyst support, average particle size: 96 μm) was ground with a ball mill, and further sieved with a dry vibration sieve to obtain catalyst particulates having a particle size of 10 μm or less.

The obtained catalyst particulates was dispersed in a hydrocarbon medium including a wax (FT wax with a content of normal paraffins having $C_{20}$ to $C_{100}$ being 99% by mass) to prepare standard samples each having a different particulate content based on the mass of the hydrocarbon medium.

[Measurement of Visible Light Transmittance]

Each of the above-described standard samples was heated to 100° C. to hold hydrocarbons in a melt state, and 5 ml of the sample was introduced in a quartz glass cell with stirring. Then, after each sample was left to stand for 10 minutes, each visible light transmittance was measured at a position which was 1 cm deeper than a liquid level of the sample by using a Visible/UV light spectrometric analysis apparatus V-660 manufactured by JASCO Corporation. Here, a measurement wavelength was 550 nm, and a temperature of the sample during the measurement was held at 100° C.

[Preparation of Calibration Curve]

Figure 3:
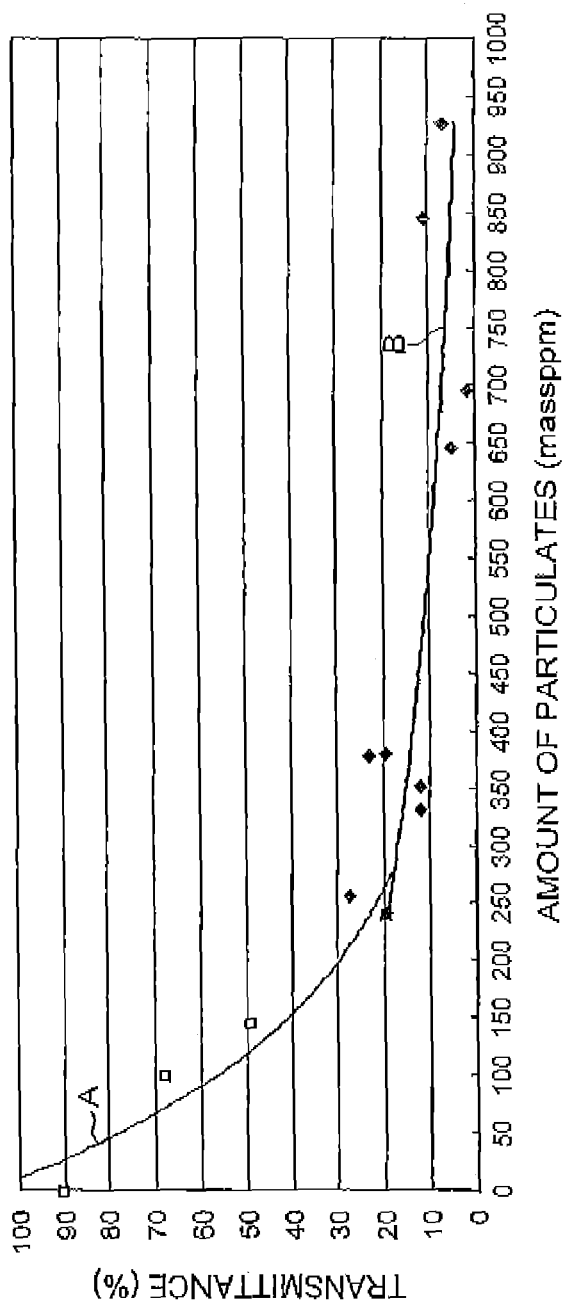
FIG. 3 is a graph plotting a relationship between a concentration of particulates in a standard sample and a visible light transmittance.

By plotting a relationship between a concentration of particulates in each standard sample and the visible light transmittance obtained as described above, a calibration curve was prepared. FIG. 3 is a graph plotting a relationship between a concentration of particulates in the standard sample and a visible light transmittance. A line indicated by A in FIG. 3 shows a calibration curve ($y=106.97e^{-0.0064x}$) prepared based on Lambert-Beer law from a result of the sample with a concentration of particulates of below 250 ppm by mass, and a line indicated by B shows a calibration curve ($y=32.641e^{-0.0022x}$) prepared based on Lambert-Beer law from a result of the sample with a concentration of particulates of 250 ppm by mass or more.

[Preparation of Slurry Sample for Measurement]

An unused FT synthesis catalyst (which was the same as that used for preparing the above-mentioned standard sample) was ground with a ball mill, and further sieved with a dry vibration sieve to obtain catalyst particulates having a particle size of larger than 10 μm. On the other hand, a sample on the sieve of the dry vibration sieve was recovered to obtain catalyst particles having a particle size of larger than 10 μm.

The catalyst particulates having a particle size of 10 μm or less were mixed to the hydrocarbon medium including a wax so that a concentration thereof was 100 ppm by mass based on the mass of the hydrocarbon medium, and further, the catalyst particles having a particle size of larger than 10 μm were mixed thereto so that a concentration thereof was 10% by mass based on the mass of the hydrocarbon medium.

[Estimation of Particulate Content in Slurry]

Example 1

The slurry sample for measurement was heated to 100° C. to hold hydrocarbons in a melt state, and 5 ml of the slurry sample was introduced in a quartz glass cell with stirring. Then, after the sample was left to stand for 10 minutes, a visible light transmittance was measured at a position which was 1 cm deeper than a liquid level of the sample in the cell by using a Visible/UV light spectrometric analysis apparatus V-660 manufactured by JASCO Corporation. Here, a measurement wavelength was 550 nm, and a temperature of the sample during the measurement was kept at 100° C.

A concentration of the particulates having a particle size of 10 µm or less was determined from the obtained visible light transmittance based on the calibration curve, and it was 89 ppm by mass based on the mass of the hydrocarbon medium.

<Evaluation of Slurry by Incineration Method and Solvent Washing Method>

With respect to generation status of particulates from a catalyst which had been used in the FT synthesis reaction for a predetermined time, the slurry was treated by the following incineration method and solvent washing method and the evaluation thereof was tried.

Comparative Example 1

A slurry containing the FT synthesis catalyst (which was the same as that used for preparing the above-mentioned standard sample) and a produced oil was taken from a FT synthesis reaction column. Here, the produced oil had a composition of the FT wax in which a content of normal paraffins having $C_{20}$ to $C_{100}$ was 99% by mass.

The taken slurry sample was calcined in an electrical heating calcining furnace electrical muffle furnace under an air flowing condition at 600° C. for 3 hours. In this way, the produced oil (hydrocarbons including a wax), which would obstruct a particle size distribution measurement to be subsequently performed, was removed by incinerating.

An incinerated residue (catalyst) was recovered after calcination and suspended in a predetermined amount of distilled water (100 ml), and a particle size distribution and an average particle size were measured by a Coulter method. On the other hand, the unused FT synthesis catalyst was also measured as in the same manner.

With respect to the unused FT synthesis catalyst, a content of particulates having a particle size of 10 µm or less was 0% based on the entire mass of the catalyst. On the other hand, with respect to the incinerated residue recovered from the slurry, the result showed that a content of particulates having a particle size of 10 µm or less was 100 ppm by mass based on the mass of the hydrocarbon medium constituting the slurry.

With respect to the average particle size, while the average particle size of the unused FT synthesis catalyst was 96 µm, the average particle size of the incinerated residue recovered from the slurry was 102 µm. Increase in average particle size of the catalyst (adhesion between particles) cannot occur essentially in use under the FT synthesis reaction condition, and it is assumed that when hydrocarbons were incinerated by calcining the slurry, for example, mother particles adhere to particulates to increase an apparent particle size.

Comparative Example 2

A slurry was taken as in Comparative Example 1. The taken slurry sample was heated to 100° C. to melt hydrocarbons, an excess of heated toluene (500 ml×3 times) was added thereto, and filter paper was used to filter and wash the slurry sample. Further, toluene was replaced for normal hexane to remove toluene, and catalyst particles on the filter paper were recovered. The recovered catalyst particles were dried under reduced pressure at 60° C. for 3 hours for removing normal hexane.

In 100 ml of distilled water was suspended 0.1 g of the dried catalyst particles, and the average particle size was measured by a Coulter method.

The average particle size of the catalyst particles recovered from the slurry was 107 µm, which was larger than the average particle size of the unused FT synthesis catalyst, 96 µm. This is considered to be due to that the apparent particle size was increased because the catalyst particles aggregated on the filter paper during being dried under reduced pressure were not sufficiently encountered at the time of being dispersed in distilled water, or the removal of hydrocarbons, in particular, a wax content was not sufficient in solvent washing.

Then, the catalyst particles recovered from the slurry was subjected to an element analysis, and as a result, it was found that 1.1% by mass of carbon (as an atom) relative to the mass of the catalyst is present. This revealed that it is difficult to completely remove hydrocarbons (in particular, wax content) adsorbed in and out of pores of the catalyst in solvent washing.

Example 2

A slurry was taken as in Comparative Example 1. The taken slurry sample was heated to 100° C. to hold hydrocarbons in a melt state, and 5 ml of the slurry sample was introduced in a quartz glass cell with stirring. Then, after the sample was left to stand for 10 minutes, a visible light transmittance was measured at a position which was 1 cm deeper than a liquid level of the sample in the cell by using a Visible/UV light spectrometric analysis apparatus V-660 manufactured by JASCO Corporation. Here, a measurement wavelength was 550 nm, and a temperature of the sample during the measurement was held at 100° C.

A concentration of the particulates having a particle size of 10 µm or less was determined from the obtained visible light transmittance based on the calibration curve, and it was 120 ppm by mass based on the mass of the hydrocarbon medium.

INDUSTRIAL APPLICABILITY

According to the present invention, a method which can simply and accurately estimate a content of particulates having a predetermined particle size or less in a slurry with solid particles dispersed in hydrocarbons including a wax, and a process for producing a hydrocarbon oil, which can prevent a filter for separating a catalyst from a slurry and a filter for removing particulates accompanied with heavy liquid hydrocarbons having passed through the filter for separating and taken out, from clogging in a slurry bubble column reactor for performing the FT synthesis reaction, to efficiently produce a hydrocarbon oil can be provided.

REFERENCE SIGNS LIST

C2 . . . Slurry bubble column reactor, C4 . . . First fractionator, C6 . . . Hydrocracking apparatus, C8 . . . Middle distillate hydrotreating apparatus, C10 . . . Naphtha fraction hydrotreating apparatus, C12 . . . Second fractionator, D4 . . . Catalyst separator, D6 . . . Filtering apparatus, F1 . . . Filter, F2 . . . Filter, L5, 6 . . . Transfer line, L10 . . . Sending-back pipe, 100 . . . System for producing hydrocarbon oil.

The invention claimed is:

1. A method for estimating a content of particulates having a predetermined particle size or having a particle size less than the predetermined particle size in a slurry with solid particles dispersed in hydrocarbons including a wax, the method comprising, based on a correlation between a visible light transmittance and a content of solid particles having the predetermined particle size or having a particle size less than the predetermined particle size at a temperature at which hydrocarbons including a wax are liquefied when the solid particles having the predetermined particle size or having a particle size less than the predetermined particle size are dispersed in the hydrocarbons:

estimating a content of particulates having the predetermined particle size or having a particle size less than the predetermined particle size in the slurry from a visible light transmittance of a supernatant part when the slurry is left to stand at the temperature at which the hydrocarbons including a wax are liquefied.

2. The method for estimating a particulate content in a slurry according to claim 1, wherein the solid particle is a Fischer-Tropsch synthesis catalyst in which cobalt and/or ruthenium is supported by an inorganic oxide catalyst support.

3. A process for producing a hydrocarbon oil by a Fischer-Tropsch synthesis reaction using a slurry bubble column reactor that retains a slurry containing catalyst particles and liquid hydrocarbons inside thereof and that has a gaseous phase portion at an upper portion of the slurry, the method comprising:

flowing the slurry through a filter provided inside and/or outside of the reactor to separate the slurry into catalyst particles and heavy liquid hydrocarbons and to take out the heavy liquid hydrocarbons;

backwashing liquid hydrocarbons through the filter in a direction opposite to the flowing direction of the slurry to return the catalyst particles accumulated on the filter into a slurry bed in the reactor; and estimating a content of particulates having a predetermined particle size or having a particle size less than the predetermined particle size in the slurry by the method according to claim 1.

4. The process for producing a hydrocarbon oil according to claim 3, wherein a frequency of performing the backwashing is determined based on the estimated content of particulates having a predetermined particle size or having a particle size less than the predetermined particle size in the slurry.

5. The process for producing a hydrocarbon oil according to claim 3, wherein a time for replacing or washing the filter for removing the particulates accompanied with the heavy liquid hydrocarbons taken out is determined based on the estimated content of particulates having a predetermined particle size or having a particle size less than the predetermined particle size in the slurry.

6. A process for producing a hydrocarbon oil by a Fischer-Tropsch synthesis reaction using a slurry bubble column reactor that retains a slurry containing catalyst particles and liquid hydrocarbons inside thereof and that has a gaseous phase portion at an upper portion of the slurry, the method comprising:

flowing the slurry through a filter provided inside and/or outside of the reactor to separate the slurry into catalyst particles and heavy liquid hydrocarbons and to take out the heavy liquid hydrocarbons;

backwashing liquid hydrocarbons through the filter in a direction opposite to the flowing direction of the slurry to return the catalyst particles accumulated on the filter into a slurry bed in the reactor; and estimating a content of particulates having a predetermined particle size or having a particle size less than the predetermined particle size in the slurry by the method according to claim 2.

7. The process for producing a hydrocarbon oil according to claim 6, wherein a frequency of performing the backwashing is determined based on the estimated content of particulates having a predetermined particle size or having a particle size less than the predetermined particle size in the slurry.

8. The process for producing a hydrocarbon oil according to claim 6, wherein a time for replacing or washing the filter for removing the particulates accompanied with the heavy liquid hydrocarbons taken out is determined based on the estimated content of particulates having a predetermined particle size or having a particle size less than the predetermined particle size in the slurry.

* * * * *